(12) United States Patent
Katsuta

(10) Patent No.: US 12,119,358 B2
(45) Date of Patent: Oct. 15, 2024

(54) DETECTION DEVICE

(71) Applicant: Japan Display Inc., Tokyo (JP)

(72) Inventor: Tadayoshi Katsuta, Tokyo (JP)

(73) Assignee: Japan Display Inc., Tokyo (JP)

( * ) Notice: Subject to any disclaimer, the term of this patent is extended or adjusted under 35 U.S.C. 154(b) by 392 days.

(21) Appl. No.: 17/714,478

(22) Filed: Apr. 6, 2022

(65) Prior Publication Data

US 2022/0238578 A1 Jul. 28, 2022

Related U.S. Application Data

(63) Continuation of application No. PCT/JP2020/038211, filed on Oct. 8, 2020.

(30) Foreign Application Priority Data

Oct. 9, 2019 (JP) ................................. 2019-186138

(51) Int. Cl.
*H01L 33/00* (2010.01)
*A61B 5/1172* (2016.01)
(Continued)

(52) U.S. Cl.
CPC ...... *H01L 27/14607* (2013.01); *A61B 5/1172* (2013.01); *H01L 27/14643* (2013.01); *G06V 40/1318* (2022.01)

(58) Field of Classification Search
CPC ......... H01L 27/14607; H01L 27/14643; H01L 27/146; H01L 29/786; H01L 27/14605;
(Continued)

(56) References Cited

U.S. PATENT DOCUMENTS

| 10,381,413 B2* | 8/2019 | Yun ..................... H10K 30/451 |
| 2009/0207291 A1 | 8/2009 | Abe et al. |
| 2014/0231781 A1* | 8/2014 | Imai ....................... H10K 30/88 257/40 |

FOREIGN PATENT DOCUMENTS

| JP | 2006-173488 A | 6/2006 |
| JP | 2009-194260 A | 8/2009 |

(Continued)

OTHER PUBLICATIONS

International Search Report issued in International Patent Application No. PCT/JP2020/038211 on Dec. 22, 2020 and English translation of same. 5 pages.

(Continued)

*Primary Examiner* — Theresa T Doan
(74) *Attorney, Agent, or Firm* — K&L Gates LLP

(57) ABSTRACT

A detection device includes: a substrate; photoelectric conversion elements provided to the substrate; transistors; and signal lines each of which is between adjacent photoelectric conversion elements. Each detection element includes one of the photoelectric conversion element and the transistors adjacent to the photoelectric conversion element. A first signal line among the signal lines is between the photoelectric conversion element of a first detection element and the photoelectric conversion element of a second detection element adjacent to one side of the first detection element and is coupled to the first detection element and the second detection element. A second signal line among the signal lines is between the photoelectric conversion element of the first detection element and the photoelectric conversion element of a third detection element adjacent to another side of the first detection element and is coupled to the first detection element and the third detection element.

11 Claims, 8 Drawing Sheets

(51) Int. Cl.
   *H01L 27/146* (2006.01)
   *G06V 40/13* (2022.01)
(58) Field of Classification Search
   CPC ......... H01L 27/14614; H01L 27/14618; H01L 27/14634; H01L 27/14636; H01L 27/14641
   USPC .......................................................... 257/96
   See application file for complete search history.

(56) References Cited

FOREIGN PATENT DOCUMENTS

| | | |
|---|---|---|
| JP | 2010-187022 A | 8/2010 |
| JP | 2014-060453 A | 4/2014 |

OTHER PUBLICATIONS

Written Opinion issued in International Patent Application No. PCT/JP2020/038211 on Dec. 22, 2020. 4 pages.
Japanese Notice of Reasons of Refusal and English Translation from corresponding Japanese Patent Application No. 2019-186138, mailed Oct. 24, 2023. 8 pages.

\* cited by examiner

DETECTION DEVICE

CROSS-REFERENCE TO RELATED APPLICATION

This application claims the benefit of priority from Japanese Patent Application No. 2019-186138 filed on Oct. 9, 2019 and International Patent Application No. PCT/JP2020/038211 filed on Oct. 8, 2020, the entire contents of which are incorporated herein by reference.

BACKGROUND

1. Technical Field

What is disclosed herein relates to a detection device.

2. Description of the Related Art

Optical detection devices are known in which a plurality of photoelectric conversion elements such as positive-intrinsic-negative (PIN) photodiodes are arranged on a substrate. Such an optical detection device is used as, for example, a biometric sensor, such as a fingerprint sensor or a vein sensor, that detects biological information. The photoelectric conversion elements are separately arranged at an arrangement pitch corresponding to a resolution of detection.

Japanese Patent Application Laid-open Publication No. 2010-187022 (JP-A-2010-187022) describes a solid-state imaging device including a photodiode and a plurality of transistors in each pixel. In the solid-state imaging device described in JP-A-2010-187022, amplification transistors formed in respective pixels are symmetrically provided with a signal line coupled to the amplification transistors interposed therebetween. That is, in JP-A-2010-187022, the signal line is shared between adjacent pixels.

The optical detection devices are required to have a large aperture ratio. When the configuration described in JP-A-2010-187022 is applied to the optical detection devices, the aperture ratio is increased, but the photoelectric conversion elements and the transistors are symmetrically arranged with the signal line interposed therebetween. Consequently, the arrangement pitch of the photoelectric conversion elements may not be constant. As a result, the positional accuracy of the detection may decrease.

For the foregoing reasons, there is a need for a detection device capable of restraining the reduction in positional accuracy of the detection and increasing the aperture ratio.

SUMMARY

According to an aspect, a detection device includes: a substrate; a plurality of photoelectric conversion elements provided to the substrate and each including a semiconductor layer having a photovoltaic effect; a plurality of transistors provided for each of the photoelectric conversion elements; and a plurality of signal lines, each of which is provided between the photoelectric conversion elements adjacent to each other in a first direction, extends in a second direction intersecting the first direction, and is configured to supply a signal to any one of the photoelectric conversion elements and the transistors. Each of detection elements includes one of the photoelectric conversion element and the transistors arranged adjacent to the photoelectric conversion element in the second direction. A first signal line among the signal lines is arranged between the photoelectric conversion element of a first detection element and the photoelectric conversion element of a second detection element adjacent to one side in the first direction of the first detection element, and is coupled to the first detection element and the second detection element. A second signal line among the signal lines is arranged between the photoelectric conversion element of the first detection element and the photoelectric conversion element of a third detection element adjacent to another side in the first direction of the first detection element, and is coupled to the first detection element and the third detection element.

DETAILED DESCRIPTION

Figure 1:
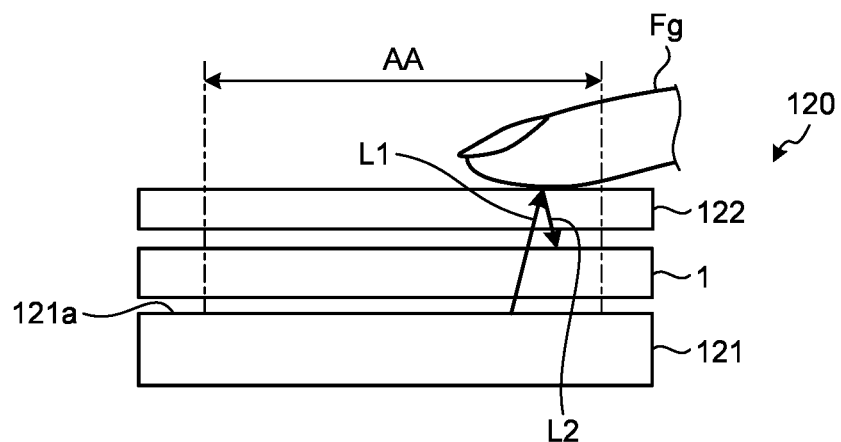
FIG. 1 is a sectional view illustrating a schematic sectional configuration of a detection apparatus with an illumination device, the detection apparatus including a detection device according to an embodiment.

The following describes a mode (embodiment) for carrying out the present disclosure in detail with reference to the drawings. The present disclosure is not limited to the description of the embodiment given below. Components described below include those easily conceivable by those skilled in the art or those substantially identical thereto. In addition, the components described below can be combined as appropriate. What is disclosed herein is merely an example, and the present disclosure naturally encompasses appropriate modifications easily conceivable by those skilled in the art while maintaining the gist of the disclosure. To further clarify the description, the drawings may schematically illustrate, for example, widths, thicknesses, and shapes of various parts as compared with actual aspects thereof. However, they are merely examples, and interpretation of the present disclosure is not limited thereto. The same component as that described with reference to an already mentioned drawing is denoted by the same reference numeral through the description and the drawings, and detailed description thereof may not be repeated where appropriate.

In the present specification and claims, in expressing an aspect of disposing another structure on or above a certain structure, a case of simply expressing "on" includes both a case of disposing the other structure immediately on the certain structure so as to contact the certain structure and a case of disposing the other structure above the certain structure with still another structure interposed therebetween, unless otherwise specified.

Embodiment

FIG. 1 is a sectional view illustrating a schematic sectional configuration of a detection apparatus with an illumination device, the detection apparatus including a detection device according to an embodiment. As illustrated in FIG. 1, a detection apparatus 120 with an illumination device includes a detection device 1, an illumination device 121, and a cover glass 122. The illumination device 121, the detection device 1, and the cover glass 122 are stacked in the order as listed, in a direction orthogonal to a surface of the detection device 1.

The illumination device 121 has a light-emitting surface 121a for emitting light and emits light L1 from the light-emitting surface 121a toward the detection device 1. The illumination device 121 is a backlight. The illumination device 121 may be, for example, what is called a side light-type backlight that includes a light guide plate provided in a position corresponding to a detection region AA and a plurality of light sources arranged at one end or both ends of the light guide plate. For example, light-emitting diodes (LEDs) for emitting light in a predetermined color are used as the light sources. The illumination device 121 may be what is called a direct-type backlight that includes the light sources (such as the LEDs) provided directly below the detection region AA. The illumination device 121 is not limited to the backlight, and may be provided on a lateral side or an upper side of the detection device 1 to emit the light L1 from the lateral side or the upper side of a finger Fg.

The detection device 1 is provided so as to face the light-emitting surface 121a of the illumination device 121. The light L1 emitted from the illumination device 121 passes through the detection device 1 and the cover glass 122. The detection device 1 is, for example, a light-reflective biometric sensor and can detect asperities (such as a fingerprint) on a surface of the finger Fg by detecting light L2 reflected on the surface of the finger Fg. Alternatively, the detection device 1 may detect information on a living body by detecting the light L2 reflected inside the finger Fg in addition to detecting the fingerprint. Examples of the information on the living body include a blood vessel image, pulsation, and a pulse wave of, for example, a vein. The color of the light L1 from the illumination device 121 may be varied depending on a detection target.

The cover glass 122 is a member for protecting the detection device 1 and the illumination device 121 and covers the detection device 1 and the illumination device 121. The cover glass 122 is, for example, a glass substrate. The cover glass 122 is not limited to a glass substrate, and may be, for example, a resin substrate. The cover glass 122 need not be provided. In this case, the surface of the detection device 1 is provided with a protective layer, and the finger Fg contacts the protective layer of the detection device 1.

The detection apparatus 120 with an illumination device may be provided with a display panel instead of the illumination device 121. The display panel may be, for example, an organic electroluminescent (EL) diode (organic light-emitting diode (OLED)) panel or an inorganic EL display (micro-LED or mini-LED) panel. Alternatively, the display panel may be a liquid crystal display (LCD) panel using liquid crystal elements as display elements or an electrophoretic display (EPD) panel using electrophoretic elements as display elements. Also, in this case, display light emitted from the display panel passes through the detection device 1, and the fingerprint of the finger Fg and the information on the living body can be detected based on the light L2 reflected by the finger Fg.

Figure 2:
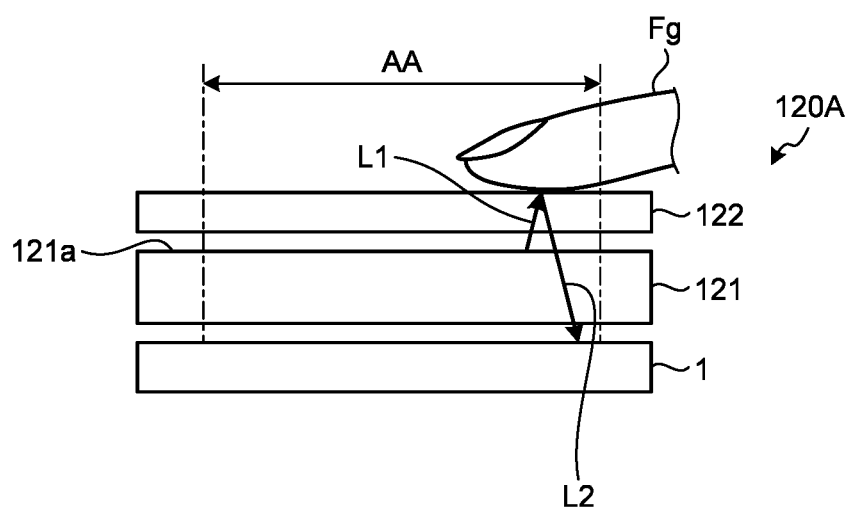
FIG. 2 is a sectional view illustrating a schematic sectional configuration of a detection apparatus with an illumination device according to a modification.

FIG. 2 is a sectional view illustrating a schematic sectional configuration of a detection apparatus with an illumination device according to a modification. As illustrated in FIG. 2, in the detection apparatus 120A with an illumination device, the detection device 1, the illumination device 121, the cover glass 122 are stacked in the order as listed, in the direction orthogonal to the surface of the detection device 1. Also, in the present modification, a display panel such as an organic EL display panel can be employed as the illumination device 121.

The light L1 emitted from the illumination device 121 passes through the cover glass 122 and then, is reflected by the finger Fg. The light L2 reflected by the finger Fg passes through the cover glass 122 and further passes through the illumination device 121. The detection device 1 can perform the detection of the information on the living body such as the fingerprint detection by receiving the light L2 that has passed through the illumination device 121.

Figure 3:
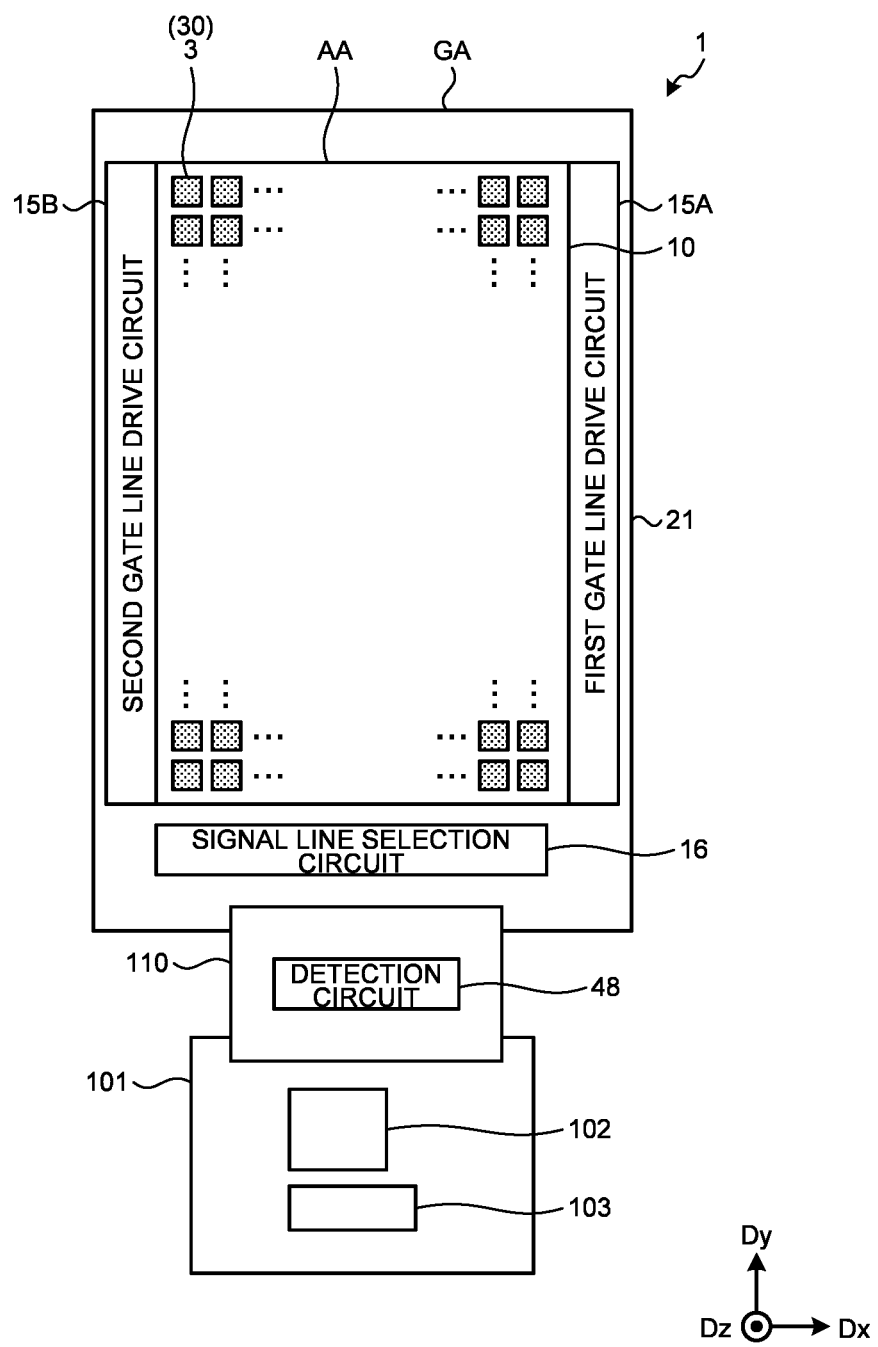
FIG. 3 is a plan view illustrating the detection device according to the embodiment.

FIG. 3 is a plan view illustrating the detection device according to the embodiment. As illustrated in FIG. 3, the detection device 1 includes a substrate 21, a sensor 10, a first gate line drive circuit 15A, a second gate line drive circuit 15B, a signal line selection circuit 16, a detection circuit 48, a control circuit 102, and a power supply circuit 103.

The substrate 21 is electrically coupled to a control substrate 101 through a wiring substrate 110. The wiring substrate 110 is, for example, a flexible printed circuit board or a rigid circuit board. The wiring substrate 110 is provided with the detection circuit 48. The control substrate 101 is provided with the control circuit 102 and the power supply circuit 103. The control circuit 102 is, for example, a field-programmable gate array (FPGA). The control circuit 102 supplies control signals to the sensor 10, the first gate line drive circuit 15A, the second gate line drive circuit 15B, and the signal line selection circuit 16 to control a detection operation of the sensor 10. The power supply circuit 103 supplies voltage signals including, for example, a power supply potential Vsf and a reference potential Vcom (refer to FIG. 5) to the sensor 10, the first gate line drive circuit 15A, the second gate line drive circuit 15B, and the signal line selection circuit 16.

The substrate 21 has the detection region AA and a peripheral region GA. The detection region AA is a region overlapping a plurality of detection elements 3 included in the sensor 10. The peripheral region GA is a region outside the detection region AA, and is a region not overlapping the detection elements 3. That is, the peripheral region GA is a region between the outer perimeter of the detection region AA and the ends of the substrate 21. The first gate line drive circuit 15A, the second gate line drive circuit 15B, and the signal line selection circuit 16 are provided in the peripheral region GA.

Each of the detection elements 3 of the sensor 10 is a photosensor including a photoelectric conversion element 30. The photoelectric conversion element 30 is a photodiode, and outputs an electrical signal corresponding to light irradiating each of the photoelectric conversion elements 30. More specifically, the photoelectric conversion element 30 is a positive-intrinsic-negative (PIN) photodiode. The detection elements 3 are arranged in a matrix having a row-column configuration in the detection region AA. The photoelectric conversion element 30 included in each of the detection elements 3 performs the detection in accordance with a gate drive signal (for example, a reset control signal RST or a read control signal RD) supplied from the first gate line drive circuit 15A or the second gate line drive circuit 15B. Each of the photoelectric conversion elements 30 outputs the electrical signal corresponding to the light irradiating the photoelectric conversion element 30 as a detection signal Vdet to the signal line selection circuit 16. The detection device 1 detects the information on the living body based on the detection signals Vdet received from the photoelectric conversion elements 30.

The first gate line drive circuit 15A, the second gate line drive circuit 15B, and the signal line selection circuit 16 are provided in the peripheral region GA. Specifically, the first gate line drive circuit 15A and the second gate line drive circuit 15B are provided in regions extending along a second direction Dy in the peripheral region GA. The signal line selection circuit 16 is provided in a region extending along a first direction Dx in the peripheral region GA, and is provided between the sensor 10 and the detection circuit 48. The first gate line drive circuit 15A and the second gate line drive circuit 15B are arranged with the detection region AA interposed therebetween in the first direction Dx. The first gate line drive circuit 15A and the second gate line drive circuit 15B are not limited to this configuration, and may be formed as one circuit and arranged along one side of the detection region AA.

The first direction Dx is one direction in a plane parallel to the substrate 21. The second direction Dy is another direction in the plane parallel to the substrate 21, and is a direction orthogonal to the first direction Dx. The second direction Dy may non-orthogonally intersect the first direction Dx. A third direction Dz is a direction orthogonal to the first direction Dx and the second direction Dy, and is a direction normal to the substrate 21.

Figure 4:
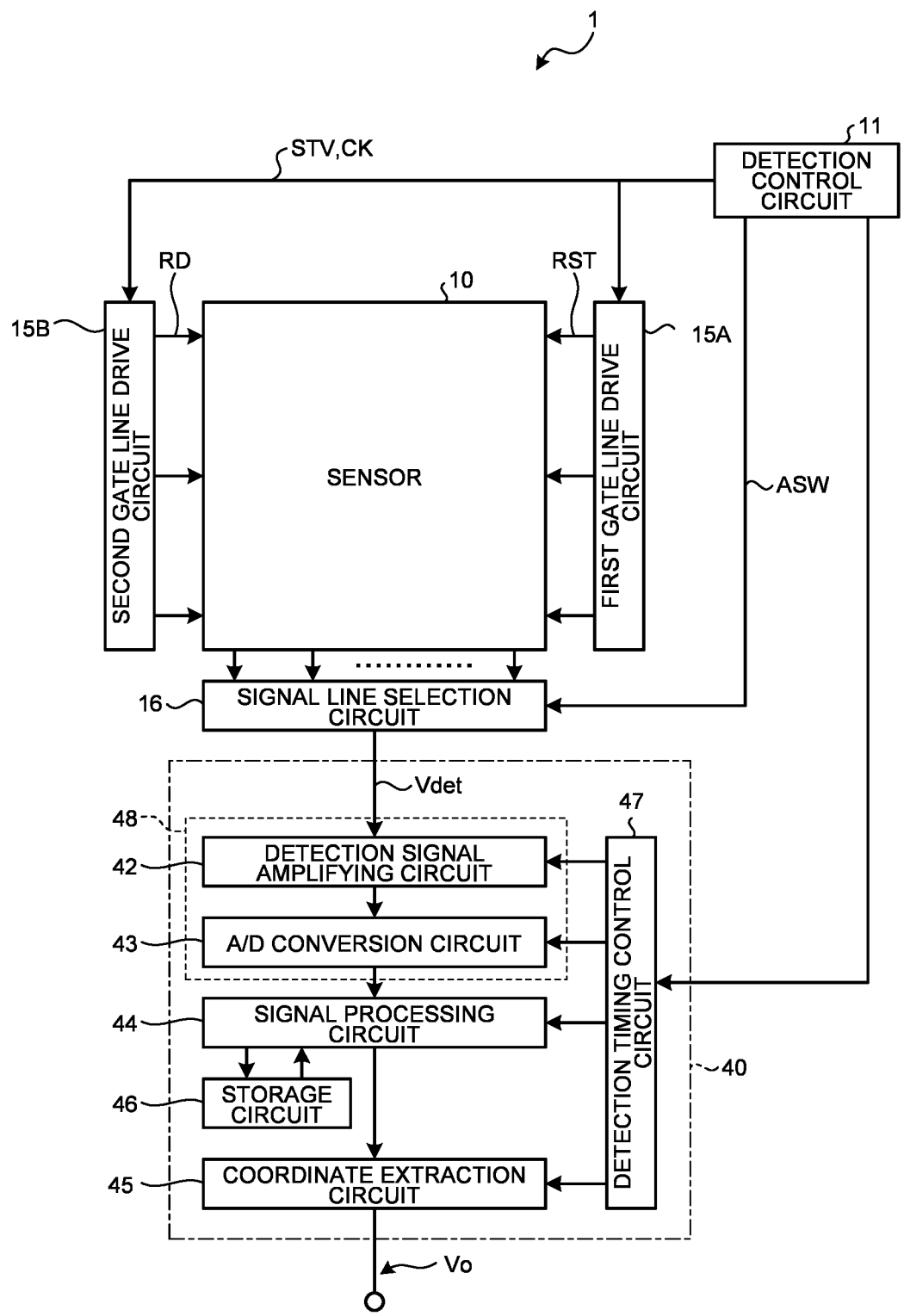
FIG. 4 is a block diagram illustrating a configuration example of the detection device according to the embodiment.

FIG. 4 is a block diagram illustrating a configuration example of the detection device according to the embodiment. As illustrated in FIG. 4, the detection device 1 further includes a detection control circuit 11 and a detector (detection signal processing circuit) 40. One, some, or all functions of the detection control circuit 11 are included in the control circuit 102. One, some, or all functions of the detector 40 other than those of the detection circuit 48 are also included in the control circuit 102.

The detection control circuit 11 is a circuit that supplies respective control signals to the first gate line drive circuit 15A, the second gate line drive circuit 15B, the signal line selection circuit 16, and the detector 40 to control operations thereof. The detection control circuit 11 supplies various control signals including, for example, a start signal STV and a clock signal CK to the first gate line drive circuit 15A and the second gate line drive circuit 15B. The detection control circuit 11 also supplies various control signals including, for example, a selection signal ASW to the signal line selection circuit 16.

The first gate line drive circuit 15A and the second gate line drive circuit 15B are circuits that drive a plurality of gate lines (read control scan lines GLrd and reset control scan lines GLrst (refer to FIG. 5)) based on the various control signals. The first gate line drive circuit 15A and the second gate line drive circuit 15B sequentially or simultaneously select the gate lines and supply the gate drive signals (for example, the reset control signals RST or the read control signals RD) to the selected gate lines. By this operation, the first gate line drive circuit 15A and the second gate line drive circuit 15B select the photoelectric conversion elements 30 coupled to the gate lines.

Figure 5:
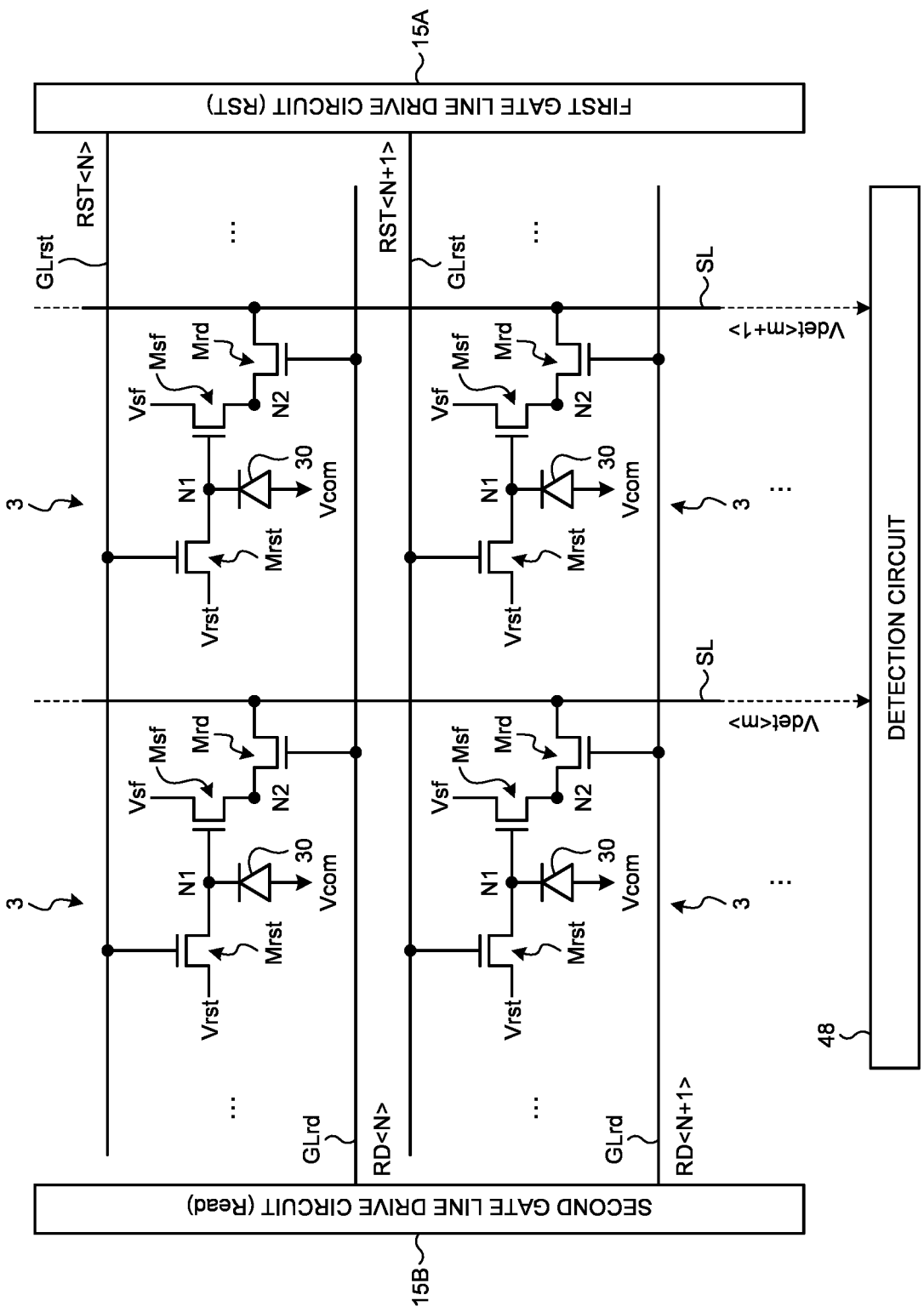
FIG. 5 is a circuit diagram illustrating a plurality of detection elements.

The signal line selection circuit 16 is a switching circuit that sequentially or simultaneously selects a plurality of output signal lines SL (refer to FIG. 5). The signal line selection circuit 16 is, for example, a multiplexer. The signal line selection circuit 16 couples the selected output signal lines SL to the detection circuit 48 based on the selection signal ASW supplied from the detection control circuit 11. Through this operation, the signal line selection circuit 16 outputs the detection signal Vdet of the photoelectric conversion element 30 to the detector 40. The signal line selection circuit 16 may be omitted. In this case, the output signal lines SL may be directly coupled to the detection circuit 48.

The detector 40 includes the detection circuit 48, a signal processing circuit 44, a coordinate extraction circuit 45, a storage circuit 46, and a detection timing control circuit 47. The detection timing control circuit 47 performs control to cause the detection circuit 48, the signal processing circuit 44, and the coordinate extraction circuit 45 to operate in synchronization with one another based on a control signal supplied from the detection control circuit 11.

The detection circuit 48 is, for example, an analog front-end (AFE) circuit. The detection circuit 48 is a signal processing circuit having functions of at least a detection signal amplifying circuit 42 and an analog-to-digital (A/D) conversion circuit 43. The detection signal amplifying circuit 42 amplifies the detection signal Vdet. The A/D conversion circuit 43 converts an analog signal output from the detection signal amplifying circuit 42 into a digital signal.

The signal processing circuit 44 is a logic circuit that detects a predetermined physical quantity received by the sensor 10 based on output signals of the detection circuit 48. The signal processing circuit 44 can detect asperities on the surface of the finger Fg or a palm based on the signals from the detection circuit 48 when the finger Fg is in contact with or in proximity to a detection surface. The signal processing circuit 44 may detect the information on the living body based on the signals from the detection circuit 48. Examples of the information on the living body include a blood vessel image, a pulse wave, pulsation, and a blood oxygen saturation level of the finger Fg or the palm.

The storage circuit 46 temporarily stores therein signals calculated by the signal processing circuit 44. The storage circuit 46 may be, for example, a random-access memory (RAM) or a register circuit.

The coordinate extraction circuit 45 is a logic circuit that obtains detected coordinates of the asperities on the surface of the finger Fg or the like when the contact or proximity of the finger Fg is detected by the signal processing circuit 44. The coordinate extraction circuit 45 is the logic circuit that also obtains detected coordinates of blood vessels of the finger Fg or the palm. The coordinate extraction circuit 45 combines the detection signals Vdet output from the respective detection elements 3 of the sensor 10 to generate two-dimensional information representing a shape of the asperities on the surface of the finger Fg or the like. The coordinate extraction circuit 45 may output the detection signals Vdet as sensor outputs Vo instead of calculating the detected coordinates.

The following describes a circuit configuration example and an operation example of the detection device 1. FIG. 5 is a circuit diagram illustrating the detection elements. As illustrated in FIG. 5, each of the detection elements 3 includes the photoelectric conversion element 30, a reset transistor Mrst, a read transistor Mrd, and a source follower transistor Msf. The detection elements 3 are provided with the reset control scan lines GLrst and the read control scan lines GLrd as detection drive lines (gate lines), and provided with the output signal lines SL as wiring for reading signals.

The reset control scan lines GLrst, the read control scan lines GLrd, and the output signal lines SL are each coupled to the detection elements 3. Specifically, the reset control scan lines GLrst and the read control scan lines GLrd extend in the first direction Dx (refer to FIG. 3), and are each coupled to the detection elements 3 arranged in the first direction Dx. The output signal lines SL extend in the second direction Dy, and are coupled to the detection elements 3 arranged in the second direction Dy. The output signal lines SL are wiring from which signals from the transistors (read transistors Mrd and source follower transistors Msf) are output.

The reset transistor Mrst, the read transistor Mrd, and the source follower transistor Msf are provided correspondingly to each of the photoelectric conversion elements 30. Each of the transistors included in the detection element 3 is fabricated from an n-type thin-film transistor (TFT). However, each of the transistors is not limited thereto, and may be fabricated from a p-type TFT.

The reference potential Vcom is applied to an anode of the photoelectric conversion element 30. A cathode of the photoelectric conversion element 30 is coupled to a node N1. The node N1 is coupled to one of the source and the drain of the reset transistor Mrst, and to the gate of the source follower transistor Msf. When light irradiates the photoelectric conversion element 30, a signal (electrical charge) output from the photoelectric conversion element 30 is stored in a capacitive element formed at the node N1.

The gate of the reset transistor Mrst is coupled to a corresponding one of the reset control scan lines GLrst. The other of the source and the drain of the reset transistor Mrst is supplied with a reset potential Vrst. When the reset transistor Mrst is turned on (into a conduction state) in response to the reset control signal RST supplied from the first gate line drive circuit 15A, the potential of the node N1 is reset to the reset potential Vrst. The reference potential Vcom is lower than the reset potential Vrst, and the photoelectric conversion element 30 is driven in a reverse bias state.

The source follower transistor Msf is coupled between a terminal supplied with the power supply potential Vsf and the read transistor Mrd (node N2). The gate of the source follower transistor Msf is coupled to the node N1. The gate of the source follower transistor Msf is supplied with a signal (voltage) corresponding to the signal (electrical charge) generated by the photoelectric conversion element 30. This operation causes the source follower transistor Msf to output a signal voltage corresponding to the signal (electrical charge) generated by the photoelectric conversion element 30 to the read transistor Mrd.

The read transistor Mrd is coupled between the source of the source follower transistor Msf (node N2) and a corresponding one of the output signal lines SL. The gate of the read transistor Mrd is coupled to a corresponding one of the read control scan lines GLrd. When the read transistor Mrd is turned on in response to the read control signal RD supplied from the second gate line drive circuit 15B, the signal output from the source follower transistor Msf, that is, the signal (voltage) corresponding to the signal (electrical charge) generated by the photoelectric conversion element 30 is output as the detection signal Vdet to the output signal line SL.

The circuit of each of the detection elements 3 is not limited to the configuration including the three transistors of the reset transistor Mrst, the source follower transistor Msf, and the read transistor Mrd. The detection element 3 may have two transistors or four or more transistors.

Figure 6:
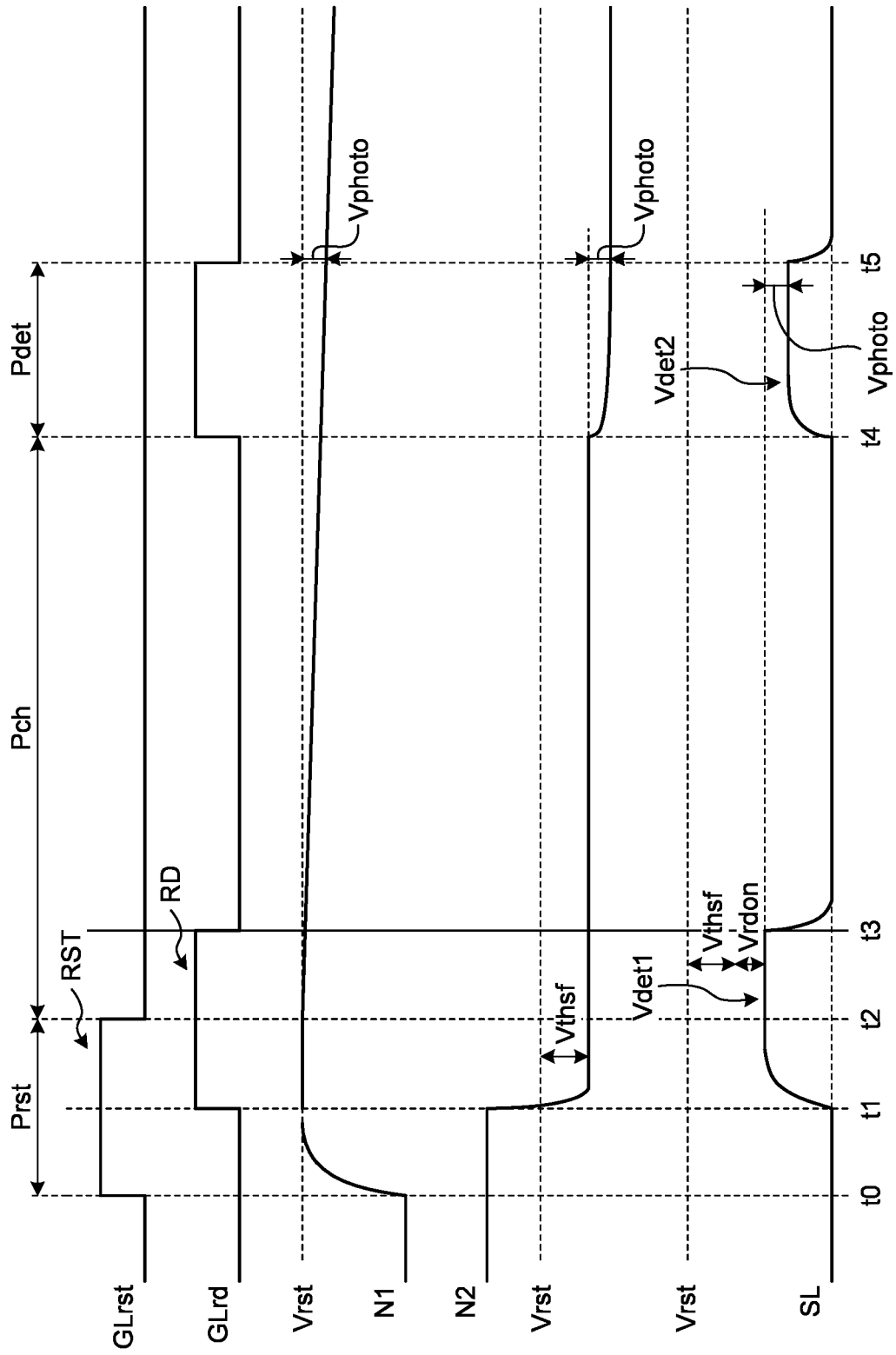
FIG. 6 is a timing waveform diagram illustrating an operation example of the detection element.

FIG. 6 is a timing waveform diagram illustrating an operation example of the detection element. As illustrated in FIG. 6, the detection element 3 performs detection in the order of a reset period Prst, a storage period Pch, and a read period Pdet. The power supply circuit 103 supplies the reference potential Vcom to the anode of the photoelectric conversion element 30 over the reset period Prst, the storage period Pch, and the read period Pdet.

At time t0, the control circuit 102 sets the reset control signal RST that is supplied to the reset control scan line GLrst to HIGH (high-level voltage) to start the reset period Prst. In the reset period Prst, the reset transistor Mrst is turned on (into the conduction state), thereby increasing the potential of the node N1 to the reset potential Vrst. The read transistor Mrd is off (in a nonconduction state). Hence, the source of the source follower transistor Msf is charged by the power supply potential Vsf, thereby increasing the potential of the node N2.

At time t1, the control circuit 102 sets the read control signal RD that is supplied to the read control scan line GLrd to HIGH (high-level voltage). As a result, the read transistor Mrd is turned on (into the conduction state), whereby the potential of the node N2 is set to (Vrst−Vthsf). Vthsf denotes a threshold voltage Vthsf of the source follower transistor Msf.

At time t2, the control circuit 102 sets the reset control signal RST to LOW (low-level voltage) to end the reset period Prst and start the storage period Pch. In the storage period Pch, the reset transistor Mrst is turned off (into the nonconduction state). The signal corresponding to the light irradiating the photoelectric conversion element 30 is stored, thereby reducing the potential of the node N1 to (Vrst−Vphoto). Vphoto denotes a signal (voltage change amount) corresponding to the light irradiating the photoelectric conversion element 30.

At time t3, the potential of a detection signal Vdet1 that is output from the output signal line SL is set to (Vrst−Vthsf−Vrdon). Vrdon denotes a voltage drop caused by on-resistance of the read transistor Mrd.

At time t3, the control circuit 102 sets the read control signal RD to LOW (low-level voltage). As a result, the read transistor Mrd is turned off (into the nonconduction state), whereby the potential of the node N2 is set to be constant at (Vrst−Vthsf). The output signal line SL is loaded so as to output the detection signal Vdet at LOW (low-level voltage).

At time t4, the control circuit 102 sets the read control signal RD(n) to HIGH (high-level voltage). As a result, the read transistor Mrd is turned on (into the conduction state) to end the storage period Pch and start the read period Pdet. The potential of the node N2 changes to (Vrst−Vthsf−Vphoto) in response to the signal Vphoto. The potential of a detection signal Vdet2 that is output in the read period Pdet decreases by an amount of the signal Vphoto from the potential of the detection signal Vdet1 obtained at time t3 and is set to (Vrst−Vthsf−Vrdon−Vphoto).

The detector 40 can detect the light irradiating the photoelectric conversion element 30 based on the signal (Vphoto) of the difference between the detection signal Vdet1 at time t3 and the detection signal Vdet2 at time t5. While FIG. 6 illustrates the operation example of one of the detection elements 3, the first gate line drive circuit 15A and the second gate line drive circuit 15B can cause the detection elements 3 in the entire detection region AA to perform the detection by sequentially scanning the reset control scan lines GLrst and the read control scan lines GLrd in a time-division manner.

Figure 7:
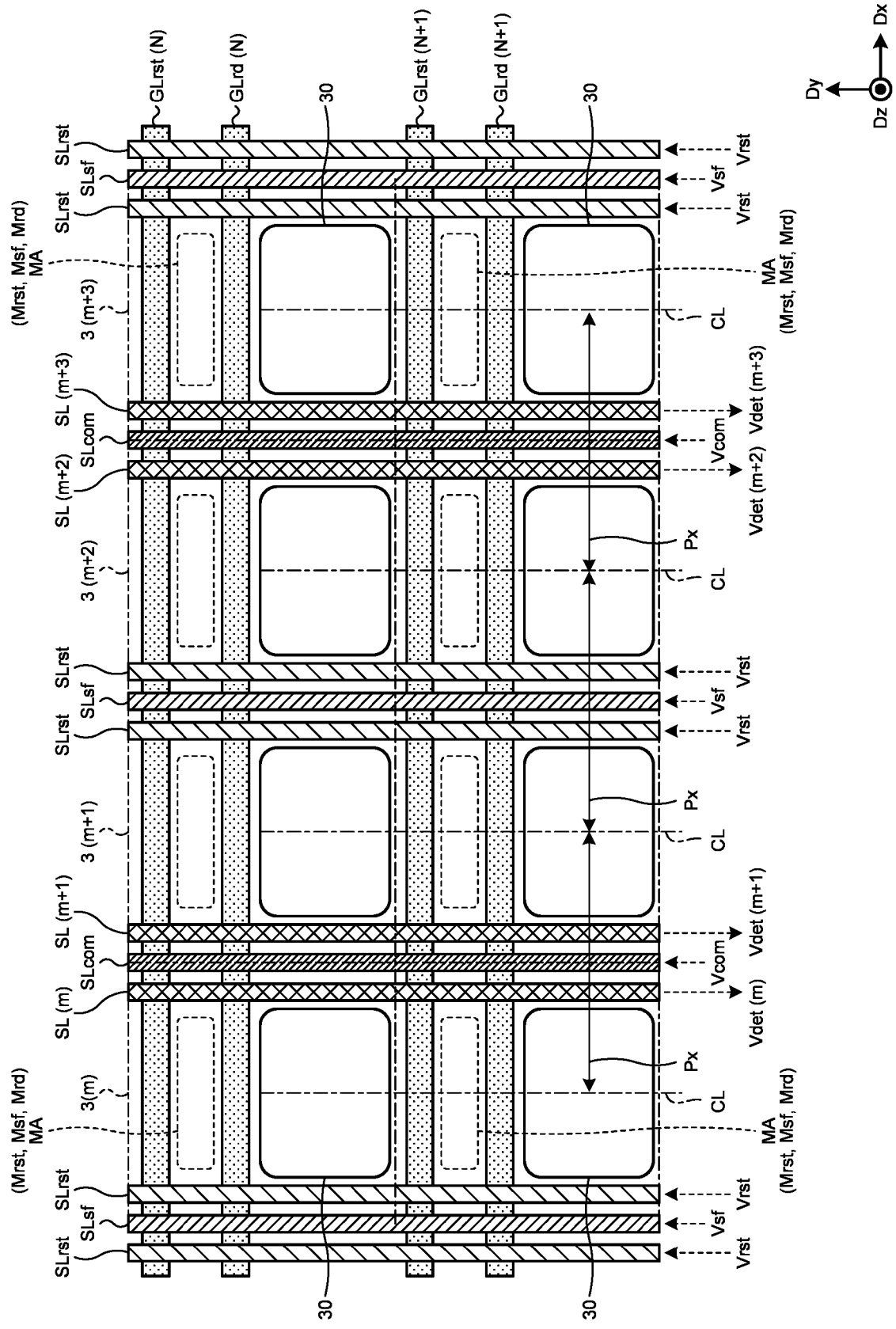
FIG. 7 is a plan view illustrating the detection elements.

The following describes a planar configuration and a sectional configuration of the detection elements 3. FIG. 7 is a plan view illustrating the detection elements. As illustrated in FIG. 7, the detection elements 3 are arranged in the first direction Dx and the second direction Dy. The detection elements 3 arranged in the first direction Dx are denoted as detection elements 3(m), 3(m+1), 3(m+2), and 3(m+3).

However, the detection elements 3(*m*), 3(*m*+1), 3(*m*+2), and 3(*m*+3) will each be simply referred to as the detection element 3 when they need not be distinguished from one another. The output signal lines SL, the read control scan lines GLrd, and the reset control scan lines GLrst are also denoted in a similar manner.

Each of the detection elements 3 is coupled to two gate lines (the read control scan line GLrd and the reset control scan line GLrst) and four signal lines (the output signal line SL, a power supply signal line SLsf, a reset signal line SLrst, and a reference signal line SLcom), and includes portions of these lines. The read control scan line GLrd and the reset control scan line GLrst extend in the first direction Dx and are arranged in the second direction Dy. The signal lines (the output signal line SL, the power supply signal line SLsf, the reset signal line SLrst, and the reference signal line SLcom) extend in the second direction Dy and are arranged in the first direction Dx.

In the example illustrated in FIG. 7, the detection element 3 is a region surrounded by the two gate lines (reset control scan lines GLrst(N) and GLrst(N+1)) and the two signal lines (the power supply signal line SLsf and the reference signal line SLcom).

Each of the detection elements 3 includes the photoelectric conversion element 30 and the transistors (the reset transistor Mrst, the read transistor Mrd, and the source follower transistor Msf) arranged adjacent to the photoelectric conversion element 30 in the second direction Dy.

The photoelectric conversion element 30 is provided in a region surrounded by the read control scan line GLrd, the reset control scan line GLrst, the reset signal line SLrst, and the output signal line SL. The transistors are arranged between the read control scan line GLrd and the reset control scan line GLrst adjacent to each other in the second direction Dy. In FIG. 7, a region in which the transistors are formed is illustrated by a dotted line as a region MA.

Each of the three signal lines (the power supply signal line SLsf, the reset signal line SLrst, and the reference signal line SLcom) other than the output signal line SL is provided between the two photoelectric conversion elements 30 adjacent to each other in the first direction Dx, extends in the second direction Dy intersecting the first direction Dx, and supplies a signal to any one of the photoelectric conversion element 30 and the transistors. For example, an output signal line SL(m), the reference signal line SLcom, and an output signal line SL(m+1) are arranged between the two photoelectric conversion elements 30 adjacent in the first direction Dx. The reset signal line SLrst, the power supply signal line SLsf, and the reset signal line SLrst are arranged between the two photoelectric conversion elements 30 adjacent in the first direction Dx. Specifically, the reference signal line SLcom supplies the reference potential Vcom to the photoelectric conversion element 30. The power supply signal line SLsf supplies the power supply potential Vsf to the source follower transistor Msf. The reset signal line SLrst supplies the reset potential Vrst to the reset transistor Mrst.

The output signal lines SL(m), SL(m+1), SL(m+2), and SL(m+3) are provided corresponding to the detection elements 3(*m*), 3(*m*+1), 3(*m*+2), and 3(*m*+3). Each of two signal lines (for example, the power supply signal line SLsf and the reference signal line SLcom) of the three signal lines other than the output signal line SL is coupled to the two detection elements 3 on both adjacent sides.

For example, describing the detection elements 3(*m*+1) and 3(*m*+2), the power supply signal line SLsf (first signal line) among the three signal lines described above is arranged between the photoelectric conversion element 30 of the detection element 3(*m*+1) (first detection element) and the photoelectric conversion element 30 of the detection element 3(*m*+2) (second detection element) adjacent to one side in the first direction Dx of the detection element 3(*m*+1). The power supply signal line SLsf is coupled to the two detection elements 3(*m*+1) and 3(*m*+2).

The reference signal line SLcom (second signal line) among the three signal lines described above is arranged between the photoelectric conversion element 30 of the detection element 3(*m*+1) and the photoelectric conversion element 30 of the detection element 3(*m*) (third detection element) adjacent to the other side in the first direction Dx of the detection element 3(*m*+1). The reference signal line SLcom is coupled to the two detection elements 3(*m*) and 3(*m*+1).

The two adjacent detection elements 3 are inverted to each other with respect to a virtual line parallel to the second direction Dy serving as an axis of symmetry. For example, the two detection elements 3(*m*) and 3(*m*+1) are symmetrical with the reference signal line SLcom interposed therebetween. The two detection elements 3(*m*+1) and 3(*m*+2) are symmetrical with the power supply signal line SLsf interposed therebetween. The two detection elements 3(*m*+2) and 3(*m*+3) are symmetrical with the reference signal line SLcom interposed therebetween.

More specifically, in the detection element 3(*m*), the power supply signal line SLsf, the reset signal line SLrst, the photoelectric conversion element 30 (and the transistors), the output signal line SL(m), and the reference signal line SLcom are arranged in the order as listed, in the first direction Dx. In the detection element 3(*m*+1), the reference signal line SLcom, the output signal line SL(m+1), the photoelectric conversion element 30 (and the transistors), the reset signal line SLrst, and the power supply signal line SLsf are arranged in the order as listed, in the first direction Dx. In the same manner, the order of arrangement of the signal lines is inverted between the detection elements 3(*m*+1) and 3(*m*+2). The reference signal line SLcom is arranged between the two output signal lines SL(m) and SL(m+1) adjacent to each other in the first direction Dx. The power supply signal line SLsf is provided between the two reset signal lines SLrst adjacent to each other in the first direction Dx.

In the detection elements 3 arranged in the first direction Dx, the photoelectric conversion elements 30 are arranged at an equal arrangement pitch Px in the first direction Dx. The arrangement pitch Px is a distance between virtual lines CL, each of which passes through a midpoint of the photoelectric conversion element 30 in the first direction Dx and is parallel to the second direction Dy. Each of the photoelectric conversion elements 30 has an external shape that is symmetrical with respect to the virtual line CL serving as an axis of symmetry. In the present specification, the term "equal" includes substantially equal.

Furthermore, in each of the detection elements 3, the photoelectric conversion element 30 is arranged between two signal lines (for example, the power supply signal line SLsf and the reset signal line SLrst) and two signal lines (for example, the output signal line SL and the reference signal line SLcom) in the first direction Dx. As a result, in each of the detection elements 3, a region occupied by the four signal lines is symmetrical with respect to the virtual line CL serving as the axis of symmetry.

As described above, the detection device 1 of the present embodiment can improve the aperture ratio of the detection element 3 by sharing the two signal lines between the two adjacent detection elements 3. For example, the aperture ratio increases by approximately 15% when compared with a configuration in which the four signal lines (the output signal line SL, the power supply signal line SLsf, the reset signal line SLrst, and the reference signal line SLcom) are provided for each of the detection elements 3. In the present specification, the aperture ratio refers to a ratio of a region not overlapping wiring and the transistors to a region surrounded by the two gate lines (the reset control scan lines GLrst(N) and GLrst(N+1)) and the two signal lines (for example, the power supply signal line SLsf and the reference signal line SLcom).

The arrangement pitches Px of the photoelectric conversion elements 30 are equal, and in each of the detection elements 3, the photoelectric conversion element 30 and the signal lines are symmetrically configured with respect to the virtual line CL serving as the axis of symmetry. This configuration allows the detection device 1 to restrain reduction in positional accuracy of the detection as compared with a case where the arrangement pitches Px are unequally provided, for example, a case where the photoelectric conversion element 30 and the transistors are arranged adjacent to each other in the first direction Dx and share the signal lines.

Figure 8:
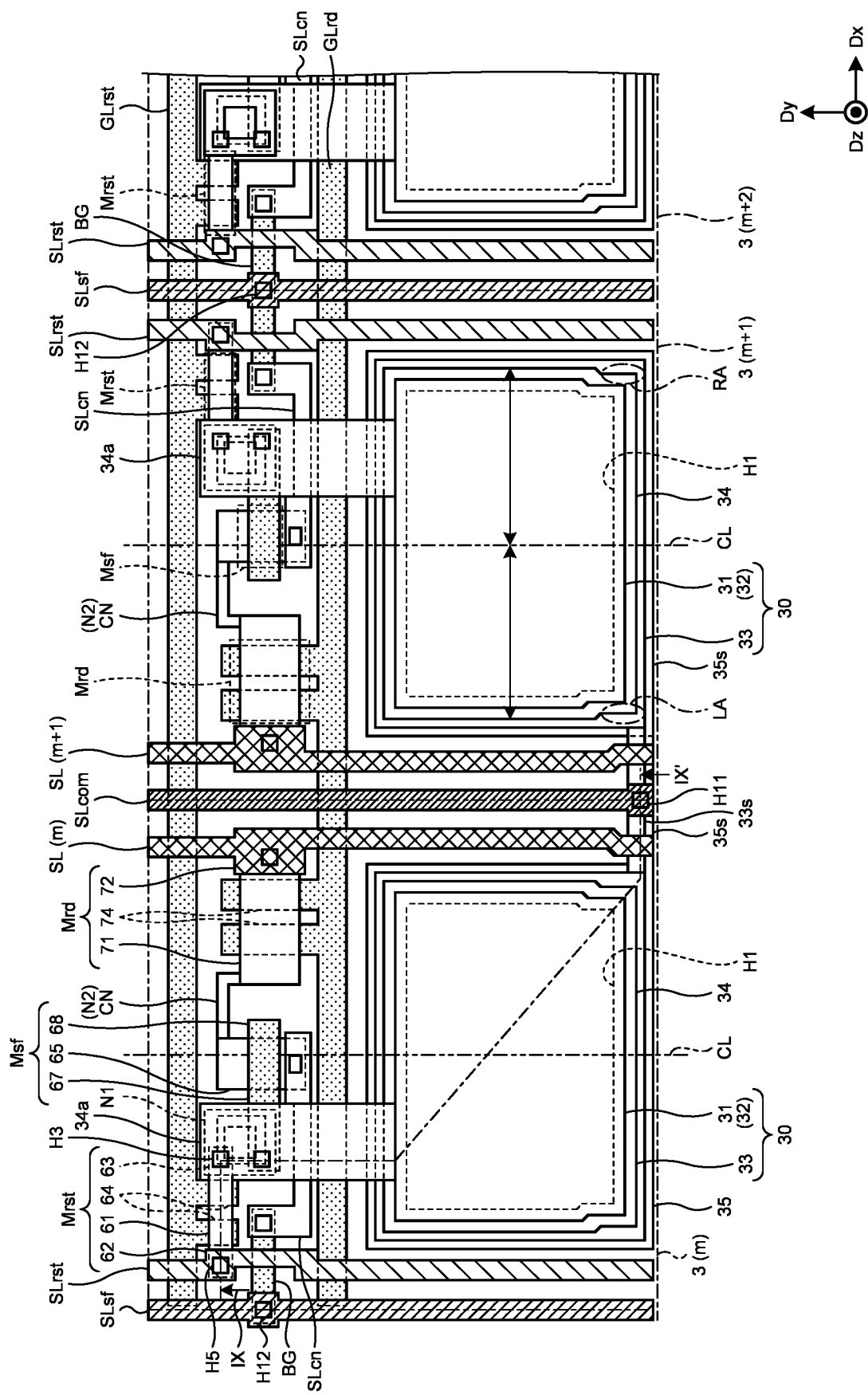
FIG. 8 is an enlarged plan view illustrating the adjacent detection elements.

FIG. 8 is an enlarged plan view illustrating the adjacent detection elements. FIG. 8 illustrates an enlarged view of the detection elements 3($m$), 3($m$+1), and 3($m$+2) that are adjacent to one another. As illustrated in FIG. 8, the photoelectric conversion element 30 includes a semiconductor layer having a photovoltaic effect. Specifically, the semiconductor layer of the photoelectric conversion element 30 includes an i-type semiconductor layer 31, an n-type semiconductor layer 32, and a p-type semiconductor layer 33. The i-type semiconductor layer 31, the n-type semiconductor layer 32, and the p-type semiconductor layer 33 are formed of, for example, amorphous silicon (a-Si). The material of the semiconductor layers is not limited thereto, and may be, for example, polysilicon or microcrystalline silicon.

The a-Si of the n-type semiconductor layer 32 is doped with impurities to form an n+ region. The polysilicon of the p-type semiconductor layer 33 is doped with impurities to form a p+ region. The i-type semiconductor layer 31 is, for example, a non-doped intrinsic semiconductor, and has lower conductivity than that of the n-type semiconductor layer 32 and the p-type semiconductor layer 33.

In the adjacent detection elements 3($m$) and 3($m$+1), the two p-type semiconductor layers 33 are coupled by coupling wiring 33$s$. The coupling wiring 33$s$ is provided so as to intersect the reference signal line SLcom, and is coupled to the reference signal line SLcom through a contact hole H11. With this configuration, the two photoelectric conversion elements 30 adjacent to each other in the first direction Dx are electrically coupled to one of the reference signal lines SLcom arranged between the two photoelectric conversion elements 30. The p-type semiconductor layers 33 of the two photoelectric conversion elements 30 are supplied with the reference potential Vcom through the common reference signal line SLcom. The two photoelectric conversion elements 30 adjacent to each other in the first direction Dx are symmetrically arranged with the reference signal line SLcom interposed therebetween.

A lower conductive layer 35 is provided in a region overlapping the semiconductor layers of the photoelectric conversion element 30. The two lower conductive layers 35 in the adjacent detection elements 3($m$) and 3($m$+1) are coupled together by coupling wiring 35$s$. The coupling wiring 35$s$ is provided so as to overlap the coupling wiring 33$s$ and intersect the reference signal line SLcom, and is coupled to the reference signal line SLcom through the contact hole H11. With this configuration, the two lower conductive layers 35 adjacent to each other in the first direction Dx are electrically coupled to one of the reference signal lines SLcom. The lower conductive layer 35 is supplied with the same reference potential Vcom as that of the p-type semiconductor layer 33, and thus, can reduce a parasitic capacitance between the lower conductive layer 35 and the p-type semiconductor layer 33. The p-type semiconductor layer 33 (coupling wiring 33$s$) and the lower conductive layer 35 (coupling wiring 35$s$) may be coupled to the common reference signal line SLcom at different positions in the second direction Dy.

The external shape of the photoelectric conversion element 30 in the plan view is symmetrically formed with respect to the virtual line CL serving as the axis of symmetry. In the detection element 3($m$+1), a recess LA is formed in the lower left corner of the photoelectric conversion element 30. The recess LA is provided so as to prevent the output signal line SL(m+1) from interfering with the photoelectric conversion element 30, for example, depending on the routing configuration of the output signal line SL(m+1). A recess RA is formed at a position in the lower right corner of the photoelectric conversion element 30 that is symmetrical to the position of the recess LA. This configuration improves the symmetry of the photoelectric conversion element 30 and can improve the positional accuracy of the detection.

An upper electrode 34 provided on the upper side of the photoelectric conversion element 30 is coupled to the n-type semiconductor layer 32 through a contact hole H1. Coupling wiring 34$a$ is coupled to the upper electrode 34 and extends in the second direction Dy. The coupling wiring 34$a$ is coupled to the node N1 through a contact hole. With this configuration, the cathode (n-type semiconductor layer 32) of the photoelectric conversion element 30 is electrically coupled to the reset transistor Mrst and the source follower transistor Msf through the coupling wiring 34$a$ and the node N1. For example, a multilayered structure of molybdenum (Mo) and aluminum (Al) can be employed as the coupling wiring 34$a$. However, the present disclosure is not limited thereto. The coupling wiring 34$a$ may be made of another metal material, and may be made of a light-transmitting conductive material such as indium tin oxide (ITO).

The reset transistor Mrst, the source follower transistor Msf, and the read transistor Mrd are adjacent to the photoelectric conversion element 30 in the second direction Dy with the read control scan line GLrd interposed therebetween. The three transistors are arranged in the first direction Dx.

The reset transistor Mrst includes a semiconductor layer 61, a source electrode 62, a drain electrode 63, and a gate electrode 64. One end of the semiconductor layer 61 is coupled to the reset signal line SLrst. The other end of the semiconductor layer 61 is coupled to the node N1 through a contact hole H3. A portion of the reset signal line SLrst coupled to the semiconductor layer 61 serves as the source electrode 62, and a portion of the node N1 coupled to the semiconductor layer 61 serves as the drain electrode 63. The gate electrode 64 is formed by branching in the second direction Dy from the reset control scan line GLrst and intersects the semiconductor layer 61. A channel region is formed in a portion of the semiconductor layer 61 that overlaps the gate electrode 64.

The source follower transistor Msf includes a semiconductor layer 65, a source electrode 67, and a gate electrode 68. One end of the semiconductor layer 65 is coupled to coupling wiring SLcn through a contact hole. The coupling wiring SLcn is electrically coupled to the power supply signal line SLsf through bridge wiring BG and a contact hole H12. The bridge wiring BG is provided in the same layer as that of, for example, the gate line (such as the read control scan line GLrd), and intersects the reset signal line SLrst in the plan view. The other end of the semiconductor layer 65 is coupled to a semiconductor layer 71 of the read transistor Mrd through coupling wiring CN (node N2).

The read transistor Mrd includes the semiconductor layer 71, a drain electrode 72, and gate electrodes 74. While FIG. 8 illustrates the semiconductor layer 71 separately from the coupling wiring CN and the semiconductor layer 65, the semiconductor layer 65, the semiconductor layer 71, and the coupling wiring CN are formed from one continuous semiconductor layer. The other end of the semiconductor layer 71 is coupled to the output signal line SL. In other words, a portion of the coupling wiring CN (node N2) coupled to the semiconductor layer 71 serves as a source electrode, and a portion of the output signal line SL coupled to the semiconductor layer 71 serves as the drain electrode 72. The two gate electrodes 74 are portions provided by branching from the read control scan line GLrd. The semiconductor layer 71 intersects the two gate electrodes 74 branching from the read control scan line GLrd. With the above-described configuration, the source follower transistor Msf and the read transistor Mrd are coupled to the output signal line SL.

Focusing on the adjacent detection elements 3(m) and 3(m+1), the reset transistors Mrst, the source follower transistors Msf, and the read transistors Mrd are symmetrically arranged with the reference signal line SLcom interposed therebetween.

Focusing on the adjacent detection elements 3(m+1) and 3(m+2), two pieces of the coupling wiring SLcn adjacent to each other in the first direction Dx are coupled to the common bridge wiring BG and are coupled to one of the power supply signal lines SLsf through the contact hole H12. That is, the two source follower transistors Msf adjacent to each other in the first direction Dx are coupled to one of the power supply signal lines SLsf arranged between the two source follower transistors Msf. The two source follower transistors Msf are symmetrically arranged with the power supply signal line SLsf interposed therebetween.

The planar configuration of the photoelectric conversion element 30 and the transistors illustrated in FIG. 8 is merely an example, and may be changed as appropriate. For example, the transistors are not limited to being arranged in the first direction Dx. Some of the transistors may be provided in different positions, for example, by being arranged so as to be adjacent to the other transistors in the second direction Dy.

Figure 9:
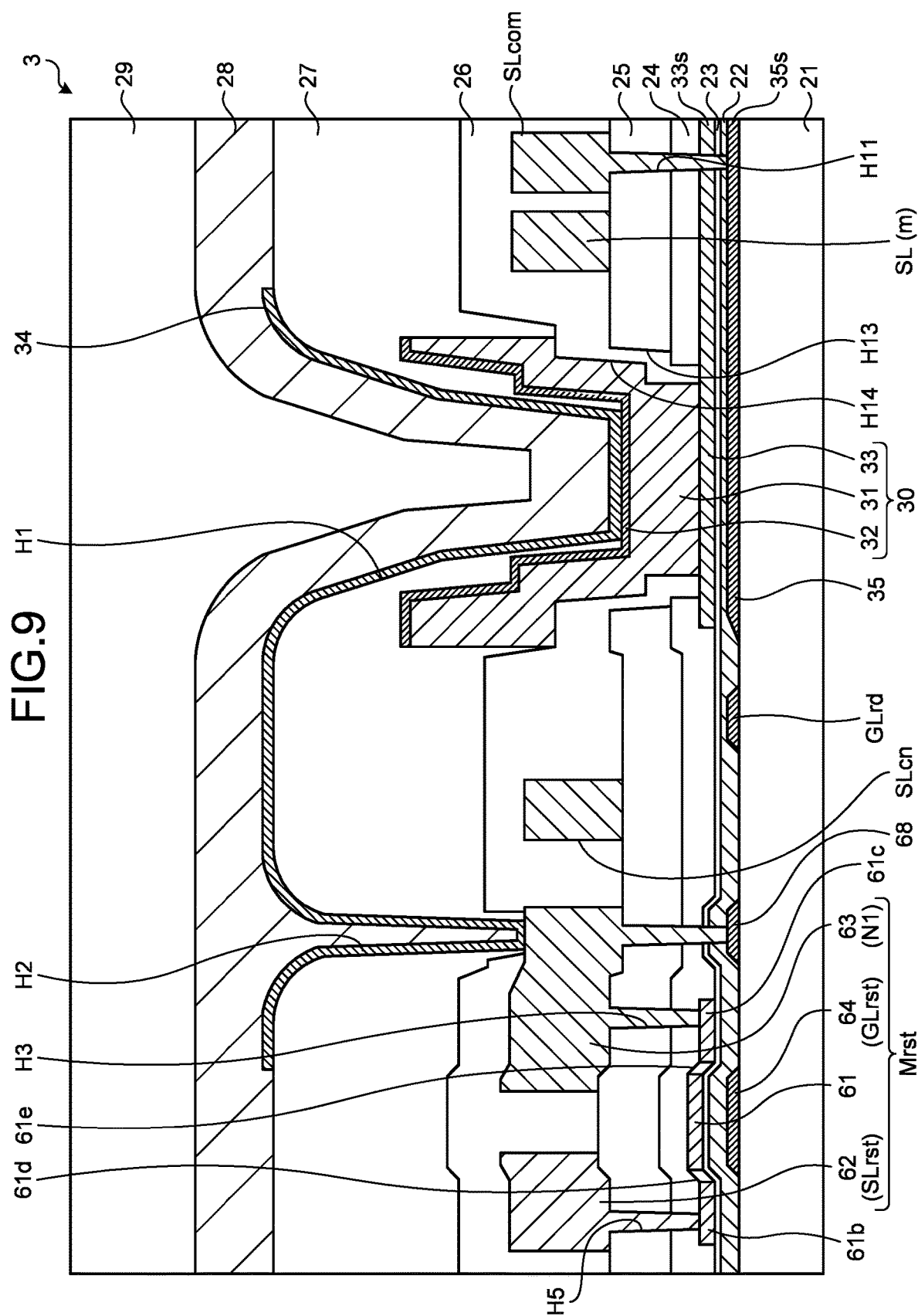
FIG. 9 is a IX-IX' sectional view of FIG. 8.

FIG. 9 is a IX-IX' sectional view of FIG. 8. While FIG. 9 illustrates a sectional configuration of the reset transistor Mrst among the three transistors included in the detection element 3, each of the source follower transistor Msf and the read transistor Mrd also has a sectional configuration similar to that of the reset transistor Mrst.

The substrate 21 is an insulating substrate. A glass substrate of, for example, quartz or alkali-free glass, or a resin substrate of, for example, polyimide is used as the substrate 21. The gate electrode 64 is provided on the substrate 21. Insulating films 22 and 23 are provided on the substrate 21 so as to cover the gate electrode 64. Insulating films 22, 23, 24, 25, and 26 are inorganic insulating films, and are formed of, for example, silicon oxide ($SiO_2$) or silicon nitride (SiN).

The semiconductor layer 61 is provided on the insulating film 23. For example, polysilicon is used as the semiconductor layer 61. The semiconductor layer 61 is, however, not limited thereto, and may be formed of, for example, a microcrystalline oxide semiconductor, an amorphous oxide semiconductor, or low-temperature polycrystalline silicon (LTPS). The reset transistor Mrst has a bottom-gate structure in which the gate electrode 64 is provided on the lower side of the semiconductor layer 61, but may have a top-gate structure in which the gate electrode 64 is provided on the upper side of the semiconductor layer 61, or a dual-gate structure in which the gate electrodes 64 are provided on the upper side and the lower side of the semiconductor layer 61.

The semiconductor layer 61 includes a channel region 61a, high impurity concentration regions 61b and 61c, and low impurity concentration regions 61d and 61e. The channel region 61a is, for example, a non-doped intrinsic semiconductor or a low-impurity region, and has lower conductivity than those of the high impurity concentration regions 61b and 61c and the low impurity concentration regions 61d and 61e. The channel region 61a is provided in a region overlapping the gate electrode 64.

The high impurity concentration region 61b is provided in a region coupled to the source electrode 62, that is, in a region overlapping a bottom surface of a contact hole H5. The high impurity concentration region 61c is provided in a region coupled to the drain electrode 63, that is, in a region overlapping a bottom surface of the contact hole H3. A low impurity concentration region 61d is provided between the channel region 61a and the high impurity concentration region 61b. A low impurity concentration region 61e is provided between the channel region 61a and the high impurity concentration region 61c.

The insulating films 24 and 25 are provided on the insulating film 23 so as to cover the semiconductor layer 61. The source electrode 62 and the drain electrode 63 are coupled to the semiconductor layer 61 through the contact holes H3 and H5 that pass through the insulating films 24 and 25. The source electrode 62 and the drain electrode 63 are formed of, for example, a multilayered film of Ti—Al—Ti layers or Ti—Al layers that has a multilayered structure of titanium and aluminum.

The gate electrode 68 of the source follower transistor Msf is provided in the same layer as that of the gate electrode 64. The drain electrode 63 (node N1) is coupled to the gate electrode 68 through a contact hole passing through the insulating films 22 to 25.

The coupling wiring SLcn is provided in the same layer as that of the source electrode 62 (reset signal line SLrst) and the drain electrode 63 (node N1).

The following describes a sectional configuration of the photoelectric conversion element 30. The lower conductive layer 35 is provided in the same layer as that of the gate electrode 64 on the substrate 21. The insulating films 22 and 23 are provided on the lower conductive layer 35. The photoelectric conversion element 30 is provided on the insulating film 23. In other words, the lower conductive layer 35 is provided between the substrate 21 and the p-type semiconductor layer 33. The lower conductive layer 35 is formed of the same material as that of the gate electrode 64 to serve as a light-blocking layer, and thus, the lower conductive layer 35 can restrain light from entering the photoelectric conversion element 30 from the substrate 21 side.

The i-type semiconductor layer 31 is provided between the p-type semiconductor layer 33 and the n-type semiconductor layer 32 in a direction orthogonal to a surface of the substrate 21 (in the third direction Dz). In the present embodiment, the p-type semiconductor layer 33, the i-type semiconductor layer 31, and the n-type semiconductor layer 32 are stacked in this order on the insulating film 23.

Specifically, the p-type semiconductor layer 33 is provided in the same layer as that of the semiconductor layer 61 on the insulating film 23. The insulating films 24, 25, and 26 are provided so as to cover the p-type semiconductor layer 33. The insulating films 24 and 25 are provided with a contact hole H13 in a position overlapping the p-type semiconductor layer 33. The insulating film 26 is provided on the insulating film 25 so as to cover the transistors including the reset transistor Mrst. The insulating film 26 covers side surfaces of the insulating films 24 and 25 constituting an inner wall of the contact hole H13. The insulating film 26 is provided with a contact hole H14 in a position overlapping the p-type semiconductor layer 33.

The coupling wiring 33s coupled to the p-type semiconductor layer 33 and the coupling wiring 35s coupled to the lower conductive layer 35 extend to positions overlapping the output signal line SL and the reference signal line SLcom, respectively. The contact hole H11 is provided through from the insulating film 22 to the insulating film 25, and the coupling wiring 33s and the coupling wiring 35s are coupled to the reference signal line SLcom through the contact hole H11.

The i-type semiconductor layer 31 is provided on the insulating film 26, and is coupled to the p-type semiconductor layer 33 through the contact hole H14 passing through the insulating films 24 to 26. The n-type semiconductor layer 32 is provided on the i-type semiconductor layer 31.

An insulating film 27 is provided on the insulating film 26 so as to cover the photoelectric conversion element 30. The insulating film 27 is provided so as to be directly in contact with the photoelectric conversion element 30 and the insulating film 26. The insulating film 27 is formed of an organic material such as a photosensitive acrylic. The insulating film 27 is thicker than the insulating film 26. The insulating film 27 has a better step covering property than that of inorganic insulating materials, and is provided so as to cover side surfaces of the i-type semiconductor layer 31 and the n-type semiconductor layer 32. The insulating film 27 may be an inorganic insulating film.

The upper electrode 34 is provided on the insulating film 27. The upper electrode 34 is formed of, for example, a light-transmitting conductive material such as ITO. The upper electrode 34 is provided along a surface of the insulating film 27 and is coupled to the n-type semiconductor layer 32 through the contact hole H1 provided in the insulating film 27. The upper electrode 34 is provided so as to cross over the upper sides of the read control scan lines GLrd and the coupling wiring SLcn, and is electrically coupled to the drain electrode 63 of the reset transistor Mrst and the gate electrode 68 through a contact hole H2 provided in the insulating film 27.

Insulating films 28 and 29 are provided on the insulating film 27 so as to cover the upper electrode 34. The insulating film 28 is an inorganic insulating film. The insulating film 28 is provided as a protective layer for restraining water from entering the photoelectric conversion element 30. The insulating film 29 is an organic protective film. The insulating film 29 is formed so as to planarize the surface of the detection device 1.

The detection device 1 of the present embodiment has been described to have the configuration in which the two adjacent detection elements 3 share the power supply signal line SLsf and the reference signal line SLcom among the three signal lines (the power supply signal line SLsf, the reset signal line SLrst, and the reference signal line SLcom) other than the output signal line SL. However, the present disclosure is not limited to this configuration.

For example, the power supply signal line SLsf and the reset signal line SLrst among the three signal lines other than the output signal line SL may be coupled to the two adjacent detection elements 3. In this case, the power supply signal line SLsf and the reset signal line SLrst are arranged with the photoelectric conversion element 30 interposed therebetween in the first direction Dx. The reference signal line SLcom is provided for each of the photoelectric conversion elements 30 arranged in the first direction Dx. The two reset transistors Mrst adjacent to each other in the first direction Dx are electrically coupled to one reset signal line SLrst arranged between the two reset transistors Mrst, and are symmetrically arranged with the reset signal line SLrst interposed therebetween.

Alternatively, the reference signal line SLcom and the reset signal line SLrst among the three signal lines other than the output signal line SL may be coupled to the two adjacent detection elements 3. In this case, the reference signal line SLcom and the reset signal line SLrst are arranged with the photoelectric conversion element 30 interposed therebetween in the first direction Dx. The power supply signal line SLsf is provided for each of the detection elements 3 arranged in the first direction Dx.

The planar configuration and the sectional configuration of the detection element 3 are merely examples and can be changed as appropriate. For example, the photoelectric conversion element 30 is not limited to the configuration including the recess LA and may have a rectangular shape, or another shape such as a polygonal shape. The order of stacking of the p-type semiconductor layer 33, the i-type semiconductor layer 31, and the n-type semiconductor layer 32 of the photoelectric conversion element 30 may be reversed. The photoelectric conversion element 30 may be provided in a layer different from that of the semiconductor layer of each of the transistors. For example, the photoelectric conversion element 30 may be provided on the insulating film 26.

While the preferred embodiment of the present disclosure has been described above, the present disclosure is not limited to the embodiment described above. The content disclosed in the embodiment is merely an example, and can be variously changed within the scope not departing from the gist of the present disclosure. Any modifications appropriately made within the scope not departing from the gist of the present disclosure also naturally belong to the technical scope of the present disclosure.

What is claimed is:

1. A detection device comprising:
a substrate;
a plurality of photoelectric conversion elements provided to the substrate and each comprising a semiconductor layer having a photovoltaic effect;
a plurality of transistors provided for each of the photoelectric conversion elements; and
a plurality of signal lines, each of which is provided between the photoelectric conversion elements adjacent to each other in a first direction, extends in a second direction intersecting the first direction, and is configured to supply a signal to any one of the photoelectric conversion elements and the transistors, wherein each of detection elements comprises one of the photoelectric conversion element and the transistors arranged adjacent to the photoelectric conversion element in the second direction,
a first signal line among the signal lines is arranged between the photoelectric conversion element of a first detection element and the photoelectric conversion element of a second detection element adjacent to one side in the first direction of the first detection element, and is coupled to the first detection element and the second detection element, and
a second signal line among the signal lines is arranged between the photoelectric conversion element of the first detection element and the photoelectric conversion element of a third detection element adjacent to another side in the first direction of the first detection element, and is coupled to the first detection element and the third detection element.

2. The detection device according to claim 1, wherein
the signal lines comprise reference signal lines configured to supply a reference potential to the photoelectric conversion elements, and
among the photoelectric conversion elements, two photoelectric conversion elements adjacent to each other in the first direction are electrically coupled to one of the reference signal lines arranged between the two photoelectric conversion elements and are symmetrically arranged with the reference signal line interposed between the two photoelectric conversion elements.

3. The detection device according to claim 2, comprising output signal lines configured to output signals from the transistors, wherein
the reference signal line is provided between two output signal lines adjacent to each other in the first direction among the output signal lines.

4. The detection device according to claim 1, wherein the photoelectric conversion elements are arranged at an equal arrangement pitch in the first direction.

5. The detection device according to claim 1, wherein an external shape of each of the photoelectric conversion elements is symmetrical with respect to a virtual line serving as an axis of symmetry that passes through a midpoint of one of the photoelectric conversion elements in the first direction and is parallel to the second direction.

6. The detection device according to claim 1, wherein
the detection element comprises a plurality of gate lines extending in the first direction and adjacent to each other in the second direction, and
the transistors are arranged between the gate lines adjacent to each other in the second direction.

7. The detection device according to claim 1, comprising output signal lines configured to output signals from the transistors, wherein
a region occupied by the signal lines and the output signal lines is symmetrical with respect to a virtual line serving as an axis of symmetry that passes through a midpoint of one of the photoelectric conversion elements in the first direction and is parallel to the second direction.

8. The detection device according to claim 1, wherein
the transistors in each of the photoelectric conversion elements comprise a source follower transistor, a reset transistor, and a read transistor,
the signal lines comprise reset signal lines configured to supply a reset signal to the reset transistors and power supply signal lines configured to supply a power supply potential to the source follower transistors, and
two of the source follower transistors adjacent to each other in the first direction are electrically coupled to one of the power supply signal lines arranged between the two source follower transistors and are symmetrically arranged with the power supply signal line interposed between the two source follower transistors.

9. The detection device according to any one of claims 1 to 7, wherein
the transistors in each of the photoelectric conversion elements comprise a source follower transistor, a reset transistor, and a read transistor,
the signal lines comprise reset signal lines configured to supply a reset signal to the reset transistors and power supply signal lines configured to supply a power supply potential to the source follower transistors, and
two of the source follower transistors adjacent to each other in the first direction are electrically coupled to one of the power supply signal lines arranged between the two source follower transistors and are symmetrically arranged with two of the reset signal lines and the power supply signal line interposed between the two source follower transistors.

10. The detection device according to claim 8, wherein each of the power supply signal lines is provided between two of the reset signal lines adjacent to each other in the first direction.

11. The detection device according to claim 9, wherein each of the power supply signal lines is provided between two of the reset signal lines adjacent to each other in the first direction.

* * * * *